Oct. 18 1949. E. PRUSHEK Plant Pat. 882
CARNATION PLANT
Filed May 16, 1947
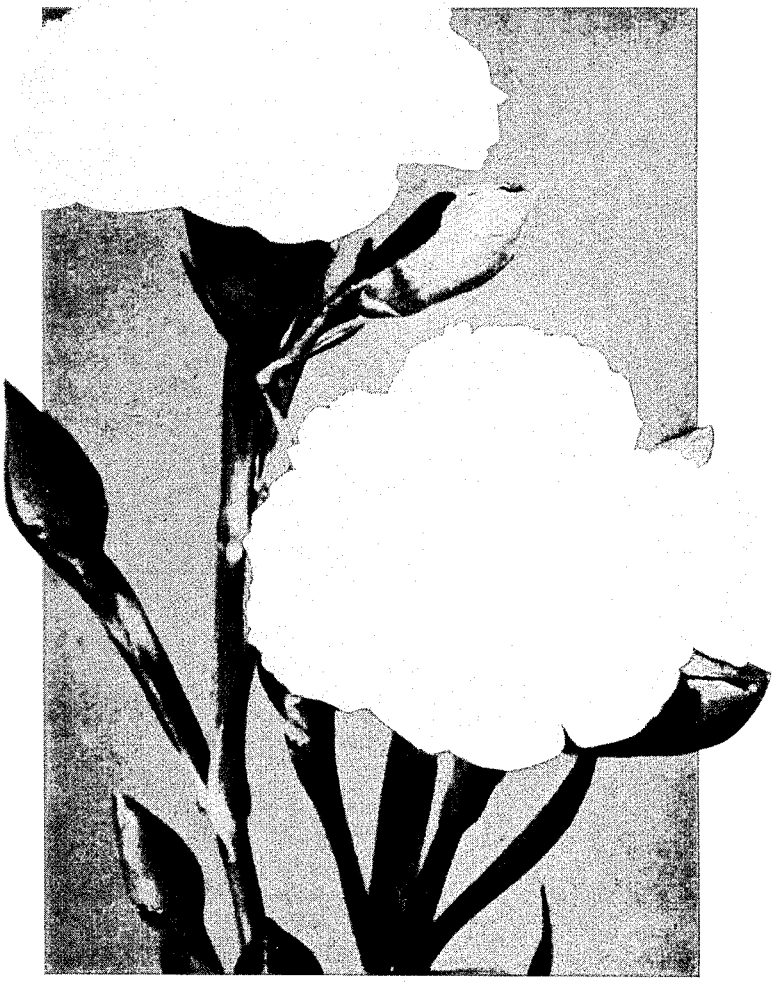
Inventor
Emil Prushek
By Robbs & Robbs
Attorneys Patented Oct. 18, 1949

Plant Pat. 882

UNITED STATES PATENT OFFICE

882

CARNATION PLANT

Emil Prushek, Niles, Mich., assignor to The R. M. Kellogg Company, Three Rivers, Mich., a corporation of Michigan Application May 16, 1947, Serial No. 748,383

1 Claim. (Cl. 47—60)

My present invention comprises a new and distinct variety of carnation plant, the result of a cross between the variety of carnation known as Spectrum Supreme and an unnamed carnation seedling resulting from a cross between *D. plumarius* and Spectrum Supreme.

A general object of my invention was to produce a new variety of carnation adapted for outdoor or garden planting which would combine the hardiness and winter survival characteristics of garden varieties with the better cut-flower characteristics of indoor or greenhouse varieties.

To the foregoing end I have conducted a program of careful selection and cross-breeding. *D. plumarius*, a garden variety outstanding for its hardiness, was crossed with Spectrum Supreme, a commercial greenhouse variety. A carefully selected seedling from this cross was back-crossed with Spectrum Supreme, resulting in the present new variety characterized by its hardy, vigorous, and compact habit of growth, its good production of side branches, its production of well-spaced flowers on stems of good cut-flower length that stand up under garden conditions, the absence of splitting of the calyx, and the pink blushing color of the flower.

My new variety does not resemble *D. plumarius* in respect to the plant form or flower, inheriting from it primarily the hardiness characteristic. The plant form of my new variety is also unlike the greenhouse parent Spectrum Supreme, my new variety being more compact, with more "breaks," or side branches, on short-jointed stems for more sprays, has better garden form, and better winter survival.

The flower of my new variety, entirely unlike that of the hardy species, *D. plumarius*, is a nearer approach to a greenhouse variety. In form the flower of my new variety is like Cheerio, but is less full. The stems of my new variety are short and stiff enough to stand up under garden conditions, which is very important. At the same time, the stems are long enough, with a few well-spaced blooms, to make a good cut-flower spray. While the flower of my new variety is fully double, the calyx is strong enough to hold it without splitting, the splitting of the calyx being a weakness of many garden and greenhouse varieties.

The pink blushing color of the flower of my new variety is distinctive, the center of the flower being pink, the base of the petals being white faintly tinged with yellow, and the outer petals being pink shading into the white of the base of the petals, with a blushing effect.

The plant form of my new variety in the garden is similar to that of Rose Unique, but is more vigorous and hardier. Compared with Rose Unique, the blooms are not as clustered, making it a better cut-flower variety. My new variety has first degree of hardiness, it is a vigorous grower, an easy propagator, and has excellent cut-flower qualities.

The plant of my new variety stands out in comparison with other hardies or with its parents particularly with reference to its compact, sturdy, and well-foliaged habit of growth, being attractive even when not in bloom. While the variety, *D. plumarius*, has the desirable characteristic of hardiness, its growth is too rank, grassy, clumpy, with far too many and too slender stems. On the other hand, the greenhouse parent is too long-stemmed, long jointed, making a top heavy, leggy plant which requires support. Hardiness, and good cut-flower qualities are not usually both found in the same variety of carnation plant, these characteristics being respectively appurtenant to two distinct types of growth. However, both of these characteristics are excellently combined in my new variety.

My new variety of carnation plant has been asexually reproduced and has been found to retain its distinctive characteristics, when so reproduced, through succeeding generations.

A typical plant of my new variety of carnation is shown in the accompanying drawing forming a part hereof.

The following is a detail description of my new variety of carnation plant, the color references being to the horticultural color chart of the British Color Council:

Parentage:

*Seed parent.*—Unnamed seedling.

*Pollen parent.*—Spectrum Supreme.

Classification: *Dianthus coryophyllus.*

*Flower*

Blooming habit: (Observations were made in the field in the county of Berrien, Michigan). Blooms are continuous.

Bud: Large in size; not effected by wet or hot weather.

Color: *Buds*—when first opening, Rhodamine Pink No. 527; when half open, Rhodamine Pink No. 527/1.

Sepals: Smooth edge.

*Bud*

Calyx: Pear-shaped; broad size.

Peduncle: Bud opens well and does not split.

*Bloom*

Size: Large. Average size when fully expanded, 2½″.

Borne: Several together; stems are medium in length; strong.

Form: When first open, high center.

Petalage: Very double; number of petals under normal conditions, 25.

Color:

*Center of flower.*—Dawn Pink No. 523.

*Outer petals.*—Dawn Pink No. 523/1.

*Base of petals.*—White, very faintly tinged with Naples Yellow, still lighter and fainter than No. 403/1.

*Inside of petals.*—Dawn Pink No. 523/1.

*Reverse of petals.*—Dawn Pink No. 523/3. Under sides of petals shade more quickly to white, with no yellow, only edges being colored.

General tonality from a distance: Dawn Pink No. 523/1. The pink shades into the white at the base of the petals, with a blushing effect.

*Petals*

Texture: Thick; soft; not affected by wet and hot weather.

Appearance: Satiny.

Form: Round; notched.

Arrangement: Informal.

Petaloids: In center, none.

Fragrance: Strong; clove.

Lastingness:

*On the plant.*—Very long.

*As cut flower.*—Very long.

*Genital organs*

Stamens: Few.

Color: Yellow.

Pollen: Lemon yellow.

Form: Bush.

Growth: Very vigorous; upright; compact.

*Foliage*

Size: Large.

Quantity: Abundant.

Color:

*New foliage.*—Upper and under sides, Scheele's Green, No. 860/3.

*Old foliage.*—Upper and under sides, Ivy Green, No. 0001060/3.

Shape: Typical carnation.

Texture: Leathery; smooth.

Edge: Smooth.

I claim:

A new and distinct variety of carnation plant characterized as to novelty by the hardy, vigorous, and compact habit of growth, its good production of side branches, its production of well-spaced flowers on stiff stems of good cut-flower length that stand up under garden conditions, the absence of splitting of the calyx, and the pink blushing color of the flowers, substantially as shown and described.

EMIL PRUSHEK.

No references cited.